United States Patent [19]

O'Neill

[11] 4,207,903
[45] Jun. 17, 1980

[54] DEVICE FOR SCREWING BODY TISSUE ELECTRODE INTO BODY TISSUE

[75] Inventor: Edward G. O'Neill, St. Paul, Minn.

[73] Assignee: Medtronic, Inc., Minneapolis, Minn.

[21] Appl. No.: 900,975

[22] Filed: Apr. 28, 1978

[51] Int. Cl.² .............................................. A61N 1/04
[52] U.S. Cl. .................................................... 128/785
[58] Field of Search .................. 128/418, 419 P, 404, 128/2.06 E, 2.1 E, 642, 784, 785, 786

[56] References Cited

U.S. PATENT DOCUMENTS

| 3,737,579 | 6/1973 | Bolduc ................................. 128/418 |
| 3,875,947 | 4/1975 | Jula et al. ............................. 128/418 |

OTHER PUBLICATIONS

Lawrie et al., "An Improved Introducer... Lead", The Annals of Thoracic Surgery, vol. 23, No. 5, May 1977.

Primary Examiner—Lee S. Cohen
Attorney, Agent, or Firm—R. Lewis Gable; Joseph F. Breimayer

[57] ABSTRACT

An assembly of a primary and an auxiliary tool employed in implanting an electrical lead and its electrode in body tissue, the primary tool or device having a groove associated therewith for holding the electrode and the lead's conductor during implantation in a manner to avoid imparting torque to the lead and undue pressure upon the body tissue during release of the lead from the primary tool. The primary tool includes a leading end with a cavity for receiving a boot for the lead's helical electrode, the groove extending longitudinally for receiving the insulated conductor, and a longitudinally extending bore which communicates the groove for receiving the auxiliary tool. The auxiliary tool includes a body portion disposable within the bore, at least one fin extending radially from its body portion and disposable within the groove, and a terminal portion moveable into the cavity. Further, the primary tool has at least one laterally disposed slot communicating with the groove for receiving the fin of the auxiliary tool, which is inserted into the bore of the primary tool and rotated so as to place its fin into the slot thus holding the auxiliary tool with respect to the primary tool. Thereafter, the electrical lead is mounted upon the primary tool by disposing its boot into the cavity and its insulated conductor into the groove. Upon urging the auxiliary tool forward, its leading end moves into the cavity removing the boot therefrom and its fin is moved into the slot thereby removing the insulated conductor from the slot.

20 Claims, 12 Drawing Figures

DEVICE FOR SCREWING BODY TISSUE ELECTRODE INTO BODY TISSUE

BACKGROUND OF THE INVENTION

1. Field of the Invention

This invention relates to the field of medical electronics and in particular to improved devices for handling electrical leads with a minimum of trauma to the body tissue in which the electrical leads are implanted.

2. State of the Prior Art

Electrical stimulation of body tissue and organs as a method of treating various pathological conditions is becoming quite commonplace. Such stimulation generally entails making some type of electrical contact with the body tissue or organ. In particular, with respect to the heart, electrical leads have been implanted by a thoracotomy in which an electrode formed on the end of the lead are physically implanted into the myocardial tissues.

Various electrode structures and various techniques for implanting those electrode structures into such body tissue as the heart or myocardium, have been developed. Typically, electrodes attached to the heart are stimulated by a cardiac pacemaker which may be implanted within the patient's body. Previously, a thoracotomy was commonly required to attach the cardiac pacemaker leads to the heart, and the electrical leads were sutured into electrical contact with the heart. This technique has numerous disadvantages. Firstly, a thoracotomy, which requires a large incision in the chest or thorax, is drastic surgery and has a relatively high mortality rate. Secondly, suturing the electrical leads into electrical contact with the heart causes severe trauma to the heart, which it is desirable to minimize.

An intravenous connection has also been used to attach electrical leads of a cardiac pacemaker to the heart. In this technique, the electrical lead is passed through a vein into the heart where it is held by fibrilla located in close proximity to the heart valve through which the lead is passed. There are, however, many disadvantages to this technique also, including: the possibility of damage to the vein during insertion, such as vein perforation; the failure to attach securely the electrical lead to the heart; the possibility of perforating the heart wall with the electrical lead during insertion or after attachment has been completed; and the possibility of improper lead placement in the heart.

In U.S. Pat. No. 3,737,579, assigned to the assignee of this invention, there is disclosed a unipolar body tissue electrode comprising an uninsulated, conductive, rigid helix adapted for attachment to body tissue and a flexible insulated conductor having a proximal end adapted for connection to a pacemaker and a distal end for connection to the helical electrode. Further, the noted patent describes a device or auxiliary tool having an elongated, cylindrical configuration. At one end thereof there is provided a slot or cavity for receiving a raised portion or boot of the lead surrounding and housing a portion of the helical electrode, and further a groove aligned with the axis of the auxiliary tool for receiving at least a portion of the length of the leads insulated conductor. The lead is mounted in the auxiliary device as indicated and the helical electrode is inserted by rotating the auxiliary tool. After the helical electrode has been inserted into the body tissue, the insulated conductor is stripped from the axially aligned groove and the boot is removed from the cavity.

In U.S. Pat. No. 3,875,947, assigned to the assignee of this invention, there is described an unipolar, tissue electrode similar to that described in U.S. Pat. No. 3,737,579, and further an improved auxiliary tool for facilitating the removal of the electrical lead from the primary tool after its helically shaped electrode has been inserted into body tissue, e.g. myocardium. In particular, the tool comprises a handle or primary tool of a substantially cylindrical configuration having a bore running along the axis thereof into which a secondary tool or tunneling rod is inserted, and a groove in communication with the bore extending also along the axis of the handle. The tunneling rod includes ridge or fin portions that are disposable in the groove and serve to remove the lead from the primary tool after electrode implantation. Further, the leading end of the tunneling rod is pointed to permit removal of the lead's boot that receives a portion of the helical electrode. In operation, the electrode is mounted as indicated above and the surgeon inserts the helical electrode by rotating the handle with the electrode mounted therein. After implantation, the surgeon inserts the tunneling rod into the bore directing the rod along the length of the handle whereby the fin is moved through the groove thus removing the lead's insulated conductor and upon full insertion, the leading end of the tunneling rod displaces the electrode's boot from the cavity.

As set out in an article entitled, "An Improved Introducer for the Sutureless Myocardial Pacemaker Lead", by Dr. Gerald M. Lawrie et al., appearing in *The Annals of Thoracic Surgery*, Volume 23, No. 5, May, 1977, a disadvantage of the inserting device of the U.S. Pat. No. 3,875,947 is that is requires a bimanual operation, i.e. the attending surgeon is required to grip the handle with one hand, while pushing forward the tunneling rod with his other hand to remove the insulated conductor. In addition, as the leading portion of the tunneling rod pushes the insulating boot of the electrode from the cavity, a rotating motion occurs, tending to displace the helical electrode within the myocardium, at right angles to the longitudinal axis of the handle. This unnecessary motion may cause myocardial trauma at the tip of the helical electrode, with subsequent fibrosis and threshold rise. To overcome these noted problems, this article suggests the adaptation of the inserting device of U.S. Pat. No. 3,875,947, by providing a series of fins in the tunneling rod and after insertion of the tunneling rod within the handling device, of placing the insulating conductor into the groove of the handle to form a plurality of loops. In addition, the leading end of the tunneling rod is shaped cylindrically whereby the attending surgeon may simply direct the tunneling rod forward with respect to the handle to remove the boot of the electrode lead, and to displace the insulated lead from the handle's slot with a single, unidirectional motion.

The forming of the loops into the noted inserting device increases the effective diameter of the device so that in a typical surgical procedure, the lead is disposed to increase the chances that it may catch on the surgeon's fingers or perhaps some portion of the exposed patient's body and be withdrawn from the groove of the inserting tool. In addition, the surgeon's attention needs to be closely directed to the relative position of the tunneling rod with respect to the handle while the lead is being inserted into the groove. In addition, after insertion, the tunneling rod is only loosely held within the handle and may through inadvertance fall out, possibly into the patient or onto the floor to be contaminated. As will be explained later, the tunneling rod may be used in a further step of the surgical procedure and if contaminated would have to be disposed.

SUMMARY OF THE INVENTION

It is therefore an object of the present invention to provide an improved implantable lead assembly for handling leads having implantable body tissue electrodes.

It is a more specific object of this invention to provide a more compact assembly of an implantable lead and lead inserting device that, when assembled, will have a minimal outside diameter which reduces interference with the surgical procedure of attaching the electrode on the lead to body tissue.

It is a further object of this invention to provide a new and improved surgical device for inserting an electrical lead that facilitates the surgical procedure and in particular permits the attending surgeon to insert the body tissue electrode with but a single hand and with a minimum of attention to the tool's operation.

In accordance with these and other objects, there is provided in accordance with the teachings of this invention a new and improved assembly for use in attaching an electrode of a body implantable electrode lead to body tissue, the lead being of a type including a flexible insulated electrical conductor having a proximal end thereof adapted for connection to a medical device, e.g., a heart pacemaker, and a distal end thereof connected to the electrode. The assembly comprises a primary device having proximal and distal ends including first means at the distal end for releasably holding an insulated portion of the electrode lead, second means extending from the proximal end to the first means for providing access therebetween, and third means for releasably holding a portion of the insulated conductor in a manner to reduce interference with the operation of attaching the electrode to body tissue. The assembly further includes an auxiliary device for insertion within the third means of the primary device and including first and second surfaces. The auxiliary device is adapted to be moved from a first position to a second position within the third means of the primary device, whereby the first surface is disposed to abut the electrode lead and to remove the electrode from the first means, and simultaneously, therewith to dispose the second surface from a third position wherein the insulated conductor is disposed within the dimensions of the primary device, to a fourth position wherein the second surface abuts and removes the portion of the insulated conductor from the third means of the primary device.

In an illustrative embodiment, the primary device takes the form of a handle having an axially aligned bore therethrough, a groove extending along the handle's axis and in communication with the bore for receiving at least a portion of the electrode lead, and a cavity disposed on the leading end of the handle for receiving the lead's boot with its helically shaped electrode disposed to be inserted within the body tissue. The auxiliary tool may take the form of a plunger that is disposable within the bore of the handle and has at least one fin or edge portion disposable into the slot. In particular, the handle has a slot disposed laterally in association with the aforementioned groove, into which the fin is placed to align accurately the tunneling rod with respect to the handle retaining same therein so that with a minimum of attention, the lead may be disposed into selected portions of the handle's groove. After electrode implantation as by rotating the handle, the lead is simply removed from the handle, by unidirectionally pressing with but a single hand the exposed rear end of the plunger forward to simultaneously remove the electrode boot from the cavity and the lead from the handle's groove.

In a further feature of this invention, the leading end of the plunger is shaped with a slight taper to be retained within a restricted portion of the handle's bore after it has been pushed forward to release the lead's boot.

In a still further feature of this invention, the handle is provided with a gripping means in the form of grooves disposed on adjacent sides of the handle to permit the attending surgeon to grip the handle with his first and forefingers while readily manipulating the end of the plunger with his thumb.

BRIEF DESCRIPTION OF THE DRAWINGS

These and other objects and advantages of the present invention will become more apparent by referring to the following detailed description and accompanying drawings, in which.

DESCRIPTION OF THE PREFERRED EMBODIMENTS

Figure 3:
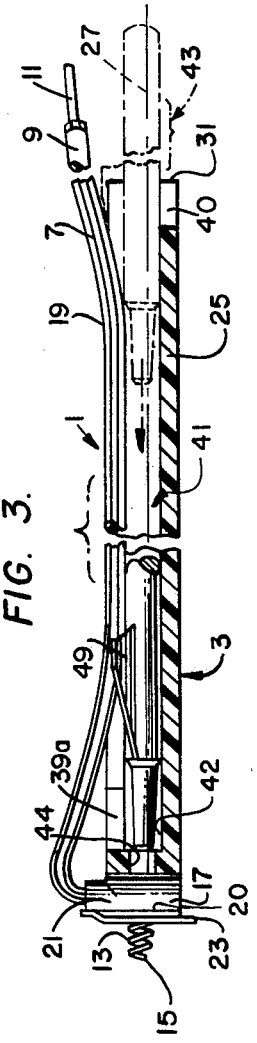
FIG. 3 is a side, sectioned view of the tunneling rod and handle of FIGS. 1 and 2, respectively, showing the manner in which the plunger is inserted into the handle's bore before the lead's insulated conductor is place into the handle's groove.

As shown in FIG. 3, an implantable lead 1 is held by a handle 3. Lead 1, which is essentially the same as lead 10 depicted in FIG. 1 of U.S. Pat. No. 3,737,579, includes a flexible conductor 7 of wrapped platinum wire or other suitable conducting material adaptable to the internal enviroment of a human or animal body.

Affixed to the proximal end of conductor 7 is an electrical connector 9 having a tip or extension 11 which may be connected to a suitable implantable or external electrical medical device. Affixed to and serving as the distal end portion of conductor 7 is a helical electrode 13 having several convolutions. Helical electrode 13 is a wire coil which may, for example, be made of platinum/iridium and terminates in a sharply pointed end 15 that is sufficiently rigid to be received into body tissue. Electrode 13 serves as the distal end portion of conductor 7 which may be screwed into body tissue as will be explained later. Electrode 13 and conductor 7 are electrically joined together by conductive epoxy (not shown) substantially orthogonally with respect to one another and this electrical junction is contained in a rubber boot 17.

Conductor 7, connector 9 and boot 17 are covered with a relatively transparent, flexible, insulating covering being relatively inert with respect to the body, which, for example, may be a silicone rubber casing 19. The portion of casing 19 surrounding boot 17 forms a raised portion or projection 21. The distal portion of casing 19 is terminated and shaped as a circular disc 20 through which helical electrode 13 projects. Helical electrode 13 projects through the disc 20 at substantially a right angle to conductor 7. Affixed to the under surface of the disc is a circular sheet of netting 23, which may, for example, be made of Dacron, a trademark of E. I. DuPont DeNemours and Company for a type of polyester fiber. Netting 23 enhances fibrotic growth, further insuring a secure connection of the electrode to the tissue.

Figure 2A:
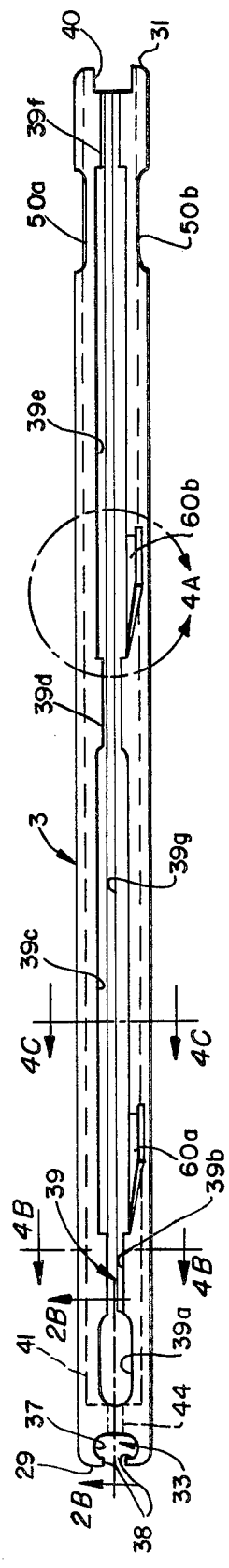
FIG. 2A shows the handle of this invention, having a bore axially disposed therein into which the plunger of FIG. 1 is disposed.

As shown in FIGS. 2A and 3, the handle 3 is adapted to hold lead 1 at two places: the boot 17 and casing 19. Handle 3 comprises a substantially cylindrically-shaped body 25 having a longitudinal axis 27 and end surfaces 29 and 31. Handle 3 may be made, for example, of a hard plastic material such as Delrin, a trademark of the E. I. DuPont DeNemours and Company for acetal resins. Preferably handle 3 should be made of an autoclavable material. Formed in end surface 29 is a slot 33. Slot 33 includes a frontal opening 35 leading to a cavity 37. The width of cavity 37 is greater than the width of frontal opening 35. The widths of frontal opening 35 and cavity 37 are selected such that boot 17 must be laterally compressed to a slight degree in order to pass through frontal opening 35. Once at least a portion of boot 17 is past the shoulders 38, that portion resumes its original shape. To remove boot 17 from slot 33 requires recompressing such portion in order to gain withdrawal from frontal opening 35. The shape of slot 33 and boot 17 is designed such that the force required to achieve the requisite compressive state is greater than the forces that might be encountered in the implantation procedure but insufficient to disturb the implanted electrode 13 as the boot 17 and slotted end 29 are being separated. Formed in the outer surface of device 3, lying in a plane substantially parallel to axis 27, and extending from end surface 31 for substantially the entire length of handle 3, is a groove 39. Groove 39, which is substantially aligned with slot 33, is adapted to receive and securely engage at least a portion of the length of casing 19. End surface 31 includes a slot 40 which communicates with a central bore 41. Central bore 41 includes a first section 42 which extends slightly beyond groove 39 and a second section 44 of reduced diameter which is concentric with section 42. Section 42 of bore 41 is adapted to receive at least a portion of the proximal end of lead 1 including connector 9 and tip 11. As will be explained in detail below, bore 41 communicates with groove 39 the entire length of groove 39.

As seen in FIG. 2A, the groove 39 is made up of various portions the functions of which will become evident by the following description. In particular, there are three narrowed portions 39b, 39d, and 39f, each of a cross-sectional dimension that is sligtly less than the cross-sectional dimension of the insulating casing 19, whereby the casing 19 of the implantable lead 1 is firmly held in these portions, 39b, 39d and 39f. The narrowed portions 39b of the groove 39 is disposed between a first portion 39a and a third portion 39c of an increased dimension. Similarly, the narrowed portion 39d is interdisposed between the portion 39c of increased and a fifth portion 39e of increased dimension, which is disposed between the portions 39d and 39f of decreased dimension. FIG. 4B shows the cross-sectional configuration of the slot 39c indicating it to have a circular configuration with curved sides 68 for holding the casing 19 therebetween. By contrast, FIG. 4c shows a cross-sectional view of the groove 38c of increased dimension, wherein the casing 19 of the lead 1 is disposed with the outer surface of the handle 3 but not tightly held. As shown in FIG. 4C, a narrowed groove 39g provides communication between the enlarged portion 39c and the axially disposed bore 41.

Figure 4A:
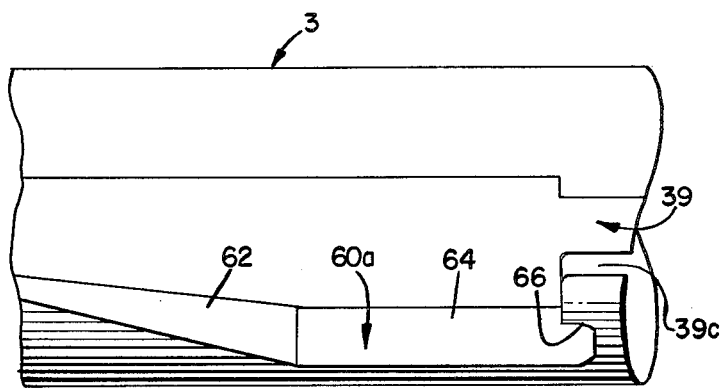
FIG. 4A is an enlarged, detailed view of the slot, as taken from the circled portion of FIG. 2.
Figure 4B:
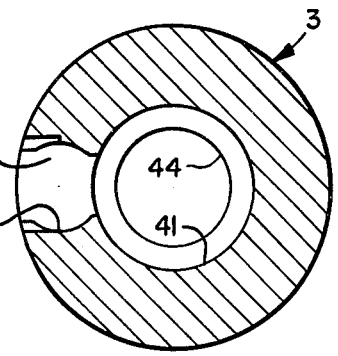
FIGS. 4B and C are sectioned views of the handle as respectively taken through lines 4B—4B of FIG. 2A and 4C—4C of FIG. 2A.
Figure 4C:
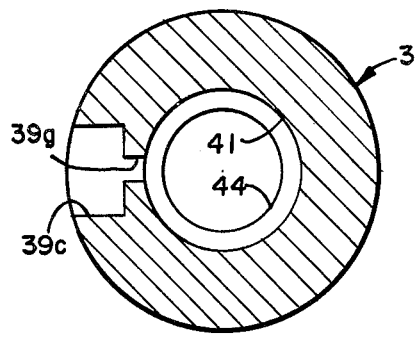

With reference to FIGS. 2A and 4A, there is shown the details of one of a plurality of laterally disposed slots 60. In particular, each slot 60 extends through the outer wall of the handle 3 into communication with the central bore 41. The slot 60 is disposed laterally of the groove 39 and includes a flat portion 64 that extends essentially parallel to the handle's axis, and a cam-like portion 62 that extends from the flat portion 64 toward the groove 39. A retaining portion 66 is an integral part of the lateral slot 60.

Figure 1:
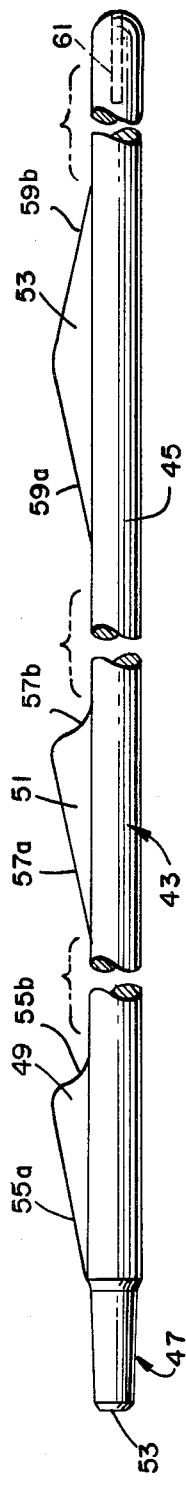
FIG. 1 is a side view of the plunger of this invention.

In FIG. 1, there is shown an auxiliary tool or plunger 43 for use in combination with the handle 3 for ejecting the lead 1 from the handle 3. The rod 43 includes a substantially cylindrical body portion 45, a leading or terminal portion 47, and a plurality of fins or edge portions 49, 51 and 53. The body portion 45 is configured and dimensioned to be inserted within and to slide freely within the axially aligned bore 41 of the handle 3. As the body portion 45 advances in the bore 41 from end 31 toward end 29, the fins 49, 51 and 53 advance within and are aligned by the groove 39. The fins 49, 51 and 53 are of such size and shape that freely slides in groove 39, i.e. the fins are preferably relatively thin, with flat, parallel side walls. Each of the fins 49, 51 and 53 have leading edges 55a, 57a and 59a respectively, that preferably slant downward to meet the body portion 45. The fin 49 has a trailing edge 55b that is similar to the trailing edge 57b of the fin 51. As will be explained, the leading edges 55a, 57a and 59a serve to remove the lead from the narrowed portions 39b, 39d and 39f of the handle 3. The fins 49 and 51 are placed by rotating the plunger 43 into the corresponding lateral slot 60a and 60b. The trailing edges 55b and 57b serve to retain the plunger 43 in a fixed position with respect to the handle 3 by engaging and being retained within the portions 66 as shown in FIG. 4A. It is understood that it is not necessary to have a third lateral slot to receive the third fin 53; thus, it is not necessary to specially configure the trailing edge 59b which may be of any configuration that is relatively easy to mold or machine. The terminal portion 47 is of reduced diameter with respect to the main portion of the tunneling rod 43 and is configured with a slightly tapered or truncated form and extends from the main portion of the plunger 43 to the leading end 53. As will be explained, the truncated portion 47 is urged into a second bore section 44 of reduced diameter with respect to that of a first section 42, whereby the tunneling rod 43 is retained within the handle 3. Further, the terminal portion 47 is of a length that will extend from the end of section 44 of the bore 41 into the cavity 33 to removed the boot 17 of the lead 1. The plunger 43 may be constructed of the same material as the handle 3.

The opposing end of the plunger 43 contains an aperture 61 leading to the outer surface of the body portion 45. Aperture 61 is provided to accommodate tip 11 of the lead 1. Though the device 43 has been described as a plunger, it may be used as a tunneling rod. In particular, after implanting the helical electrode 13 in the tissue and removing lead 1 from the handle 3, the dangling tip 11 is inserted into aperture 61 and the plunger 43 is used as a needle-like device to tunnel through subcutaneous tissue to bring lead 1 to proper position for connection at tip 11 to a suitable electrical medical device, e.g., a heart pacemaker.

Figure 5A:
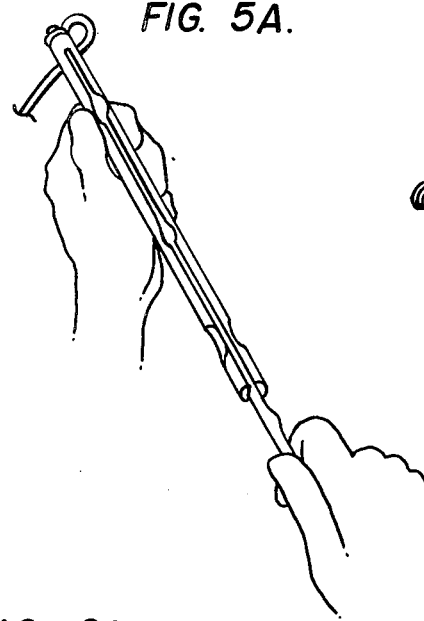
FIGS. 5A and B are pictorial representations of the manner in which the electrical lead is inserted within the device of this invention.
Figure 5B:
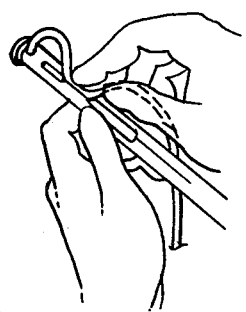
FIG. 5C is a pictorial representation of the manner in which the attending surgeon ejects the lead from the handle; and, FIGS. 6A and 6B are side views of sections of an alternative embodiment of the plunger and handle of this invention.

FIG. 3 shows the handle 3 gripping the boot 17 of the lead 1 within its cavity 33 and partially along the groove 39. Tool or tunneling rod 43 is inserted within the bore 41 with its fins disposed within the lateral slots 60a and 60b. In using the present invention, the first step is to insert the tunneling rod 43 within the bore 41 of the handle 3. Next, in a manner as illustrated in FIG. 5A, the attending physician rotates the tunneling rod 43 in a counterclockwise direction to place the fins 49 and 51 respectively into the lateral slots 60a and 60b. The lateral slots 60 serve to readily indicate the correct position of the tunneling rod 43 with respect to the handle 3, in order to receive the lead 1 as will be explained. As illustrated in FIG. 4A, the portion 66 of the slot 60 serves to retain the trailing edges 55b and 57b of the respective fins 49 and 51, to thereby hold the tunneling rod 43 within the handle 3. Next as illustrated in FIG. 5B, the surgeon places the lead 1 within the handle 3 by first inserting the boot 17 within the cavity 33 and next forming a small loop, as illustrated in FIG. 5B, inserts a portion of the casing 19 within the first restricted groove portion 39b and thereafter places the remaining portion of the casing 19 within the enlarged portion 39c, restricted portion 39d, the enlarged portion 39e, and the restricted portion 39f, whereby the casing 19 of the lead 1 is disposed substantially within the groove 39 so as not to extend beyond the outer dimensions of the handle 3. At this point, the assembly is now ready for the electrode to be screwed into body tissue.

It should be recognized that these steps of assembling the lead handle, plunger and lead together may advantageously be performed in the final process of assembly, packaging and sterilization by the manufacturer, so that the physician is presented with a sterile lead assembly ready for use in the surgical procedure now to be described.

In the surgical procedure, the pointed end 15 is placed against the tissue or organ, such as the patient's heart, and the handle is rotated, e.g. three turns, whereby the helical electrode 13 is firmly screwed into the tissue or organ until the netting 23 firmly contacts the outer surface of the organ. Netting 23 helps to provide a more secure and permanent placement of the helical electrode 13 in the tissues in that the netting 23 promotes more rapid fibrosis in and around the netting 23, as well as around the boot 17, thus avoiding the use of suturing techniques and the resultant trauma.

Figure 2B:
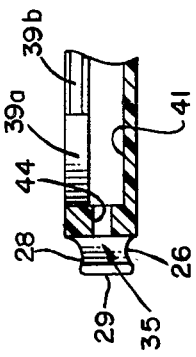
FIG. 2B shows a sectioned, side view of the leading end thereof.
Figure 5C:
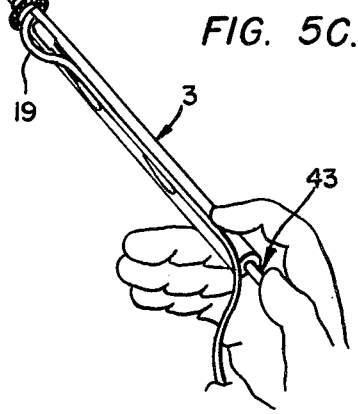

When the helical electrode 13 is firmly screwed into the tissue, the attending surgeon, illustratively with but a single hand as shown in FIG. 5C, grips the handle 3 placing his first and forefingers within the grooves 50a and 50b and his thumb against the protruding end of the plunger 43, presses it to move the plunger 43 a short unidirectional stroke in the direction of the patient's heart, while the first and forefingers prevent movement of the handle 3 toward the heart, whereby the leading end 53 of the plunger 43 extends through the narrowed section 44 and into the cavity 33 to eject the boot 17 therefrom and at the same time, the fins 49, 51 and 53 rotate as the plunger 43 advances to be disposed against the cam surfaces 62 of the lateral slots 60, thus rotating the fins in a clockwise direction as shown in FIG. 5A to bring each of the fins 49, 51 and 53 into the groove 39 whereby the casing 19 of the lead 1 is efficiently removed from the groove 39. As shown in FIG. 2B, a portion 28 of the cavity 33 is removed to facilitate the removal of the boot 17 therefrom. In addition, the tapered portion 47 of the plunger 43 has been jammed within the restricted section 44 of the handle 3 thereby retaining the plunger 43 within the handle 3 so that the rod may be used for a later step of the surgical procedure as indicated above. With the use of the described handle and rod in this procedure, no torque is transmitted to the conductor of the lead 1 and significantly, the force exerted against the heart during the step of removing the lead 1 from the handle 3, is minimized as well as the possible resultant trauma.

Figure 6A:
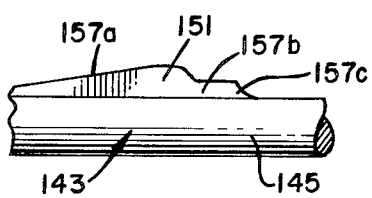
Figure 6B:
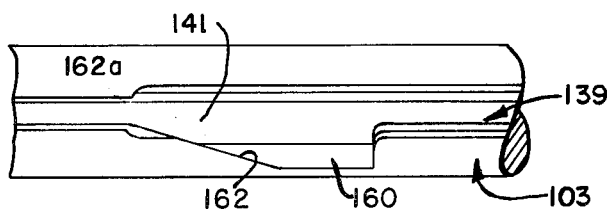

Referring now to FIGS. 6A and 6B, there is illustrated an alternative embodiment of this invention showing broken away portions respectively of the handle 103 and the plunger 143, wherein the elements are shown with nunbers corresponding to that used above but numbered in the hundred series. In particular, the plunger 143 includes a body portion 145 from which the fin 151 extends substantially radially. The fin includes a forward extending edge 157a that is used to remove the lead from the groove 139 of the handle 103, as shown in FIG. 6B. The feature of this embodiment resides in a trailing portion 157b of reduced height, which is used to retain the plunger 143 within the handle 103. In particular, as shown in FIG. 6B, the tunneling rod 145 is disposed within the central bore 141 of the handle 103 and is rotated so as to place its fin 151 within the slot 160. The slot's cam surface 162 provides a new function, i.e., as the plunger 143 is rotated, the surface 162 abuts the leading edge 157a forcing it backward whereby the raised portion 157b comes into close engagement with the inner wall of the bore 141, thereby tending to retain the plunger 143 within the bore 141 of the handle 103.

Thus, there has been disclosed a tool including a handle and a tunneling rod, whereby an electrical lead is inserted into body tissue, e.g., the patient's heart, with a minimum of force and trauma imposed thereon. The described tunneling rod includes at least one fin that is rotated to engage a lateral slot within the handle, the lateral slot serving to effectively orient the tunneling rod with respect to the handle and further, to retain the rod within the handle while the attending physician is placing the lead within the handle. Further, the surgeon is able to release the lead from the handle after the electrode has been implanted within the tissue, by a relatively simple unidirectional motion that imposes a minimum of pressure or force upon the patient's heart.

Numerous changes may be made in the above-described apparatus and the different embodiments of the invention may be made without departing from the spirit thereof; therefore, it is intended that all matter contained in the foregoing description and the accompanying drawings shall be interpreted as illustrative and not in a limiting sense.

What is claimed is:

1. An assembly for use in attaching an electrode of a body implantable lead to body tissue, said lead being of a type including a flexible insulated electrical conductor having a proximal end thereof adapted for connection to a medical device and a distal end thereof connected to said electrode, said assembly comprising:
(A) a primary device having proximal and distal ends for remotely effecting the attachment of said electrode to body tissue and including:
 1. first means at said distal end thereof for releasably holding a first insulated portion of said electrode lead for remote attachment to body tissue;
 2. second means extending from said proximal end to said first means for providing access therebetween;
 3. third means for releasably holding a portion of said insulated conductor in a manner to reduce interference with the operation of attaching said electrode to body tissue; and
 4. fourth means disposed in communication with said third means and having a cam portion;
(B) auxiliary device means for insertion within said third means of said primary device and including first and second surfaces, said auxiliary device means being disposable from a first position to a second position within said third means of said primary device whereby said first surface is disposed to abut said electrode lead and to remove said electrode from said first means of said primary device and simultaneously therewith to dispose said second surface from a third position within said fourth means wherein said insulated conductor is disposed entirely within the dimensions of said primary device, against said cam portion to a fourth position whereby said second surface abuts and removes said portion of said insulated conductor from said third means of said primary device.

2. The assembly of claim 1, wherein said second means is a bore extending axially through said primary device.

3. The assembly of claim 1, wherein said primary device is of a substantially cylindrical configuration and has an axis.

4. The assembly of claim 3, wherein said third means comprises a groove formed in an outer surface of said primary device and is disposed substantially parallel to said axis, and said second means comprises a bore disposed along said axis for substantially the entire length of said groove.

5. The assembly of claim 1, wherein said third means comprises a groove disposed substantially the entire length of said primary device and said fourth means comprises at least one slot disposed laterally of said groove and in communication therewith, said lateral slot having a first retaining portion and said cam portion.

6. The assembly of claim 5, wherein said auxiliary device means comprises an axis extending the length thereof and a fin extending substantially radially from said axis and including said second surface, said auxiliary device means being insertable within said second means of said primary device so that as it is directed in an unidirectional motion within said second means toward said first means, said second surface of said fin engages said cam portion and is disposed from said first position to said second position removing said portion of said insulated conductor from said groove.

7. The assembly of claim 6, wherein said first retaining portion engages said fin in said first position to retain said auxiliary device means within said second means of said primary device.

8. The assembly of claim 1, wherein said second means comprises a bore extending axially of and along the entire length of the said primary device and having a first section of a relatively large dimension and a second section of a relatively small dimension, said second section disposed between said first section and said first means, said auxiliary device means having a leading end that is configured to be disposed within said second section, retaining said auxiliary device means within said third means of said primary device.

9. An assembly for use in attaching an electrode of a body implantable lead to body tissue, said lead being of the type including a flexible insulated electrical conductor having a proximal end thereof adapted for connection to an electrical medical device, a distal end thereof connected to said electrode and a boot portion disposed about said electrode, said assembly comprising:
(A) a handle having proximal and distal ends and being of a substantially cylindrical configuration including a cavity disposed at said distal end thereof for receiving and holding the boot portion of said electrode lead near said uninsulated distal end portion thereof, a groove disposed along the axial length of said handle for releasably receiving and holding said insulated conductor, a bore extending axially of said handle from said distal end to said proximal end and communicating with said cavity and said groove for facilitating the release of said lead from said handle, and at least one slot disposed laterally of and in communication with said groove, said slot having a cam portion; and
(B) a plunger having a leading end thereof and at least one fin extending substantially radially therefrom, said plunger being slidably disposed within said bore of said handle, toward said cavity, whereby said fin is disposed from a first position, wherein said insulated conductor is disposed totally within the dimensions of said handle, engaging said cam portion to be moved to a second position whereby said fin abuts and removes said insulated conductor from said groove of said handle.

10. The assembly of claim 9, wherein said lateral slot includes a second retaining portion and said first mentioned cam portion.

11. The assembly of claim 9, wherein said second retaining portion engages said fin in said first position to retain said plunger within said bore of said handle.

12. The assembly of claim 9, wherein said bore extends axially of and along the entire length of said handle and includes a first section of a relatively large dimension and a second section of a relatively small dimension, said second section disposed between and intercommunicating with said first section and said cavity, said leading end of said plunger is configured to be disposed within said second section, retaining said plunger within said bore of said handle.

13. The assembly of claim 9, wherein said fin includes a leading edge surface for abutting and removing said insulated conductor and a trailing surface from which extends a raised portion, said raised portion abutting said bore of said handle when said fin is disposed in its second position to retain said plunger within said bore of said handle.

14. An assembly for use in attaching an electrode of a body implantable lead to body tissue, said lead being of the type including a flexible insulated electrical conductor having a proximal end thereof adaptable for connection to an electrical medical device and a distal end thereof connected to said electrode, said assembly comprising:

(A) handle means having proximal and distal ends for remotely effecting the attachment of said electrode to body tissue, said handle means having first means at said distal end thereof for releasably holding said electrode in a position for remote attachment to body tissue, second means extending from the proximal end to said first means for providing access therebetween, third means for releasably holding a length of said insulated electrical conductor between said proximal and distal ends of said handle means in a position along said handle means reducing interference with the operation of attaching said electrode to body tissue; and fourth means disposed in communication with said third means and having a cam portion; and (B) plunger means having proximal and distal ends for being slidably disposable from a first position to a second position along said second means by advancement of said proximal end thereof, whereby said distal end thereof may be extended to reach said first means to release said electrode therefrom, said plunger means further comprising fifth means disposed in said fourth means when said plunger means is in its first position and for engaging said cam portion to be disposed into said third means upon advancement of said plunger means to said second position, whereby said fifth means releases said length of said insulated electrical conductor from said third means.

15. The assembly of claim 14, wherein said second means is a bore extending axially through said handle means.

16. The assembly of claim 14, wherein said handle means is of a substantially cylindrical configuration and has an axis.

17. The assembly of claim 16, wherein said third means comprises a groove formed in an outer surface of said handle means and is disposed substantially parallel to said axis, and said second means comprises a bore disposed along said axis for substantially the entire length of said groove.

18. The assembly of claim 14, wherein said third means comprises a groove disposed substantially the entire length of said handle means and said fourth means comprises at least one slot disposed laterally of said groove and in communication therewith, said lateral slot having a retaining portion and said cam portion.

19. The assembly of claim 18 wherein said plunger means comprises an axis extending the length thereof and said fifth means comprises a fin extending substantially radially from said axis thereof and including a cam surface, said plunger means being insertable within said second means of said handle means so that as it is directed in a unidirectional motion within said second means toward said first means, said cam surface of said fin engages said cam portion and is disposed from said first position to said second position removing said length of said insulated conductor from said groove.

20. The assembly of claim 19, wherein said length of said insulated conductor engages said fin in said first position to retain said plunger means within said second means of said handle means.

* * * * *